United States Patent [19]

Snyder et al.

[11] Patent Number: 4,956,452

[45] Date of Patent: Sep. 11, 1990

[54] MONOCLONAL ANTIBODY WHICH NEUTRALIZES MULTIPLE STRAINS OF INFECTIOUS BURSAL DISEASE VIRUS

[75] Inventors: David B. Snyder, Lanham; Warren W. Marquardt, New Carrollton; Sammy L. Gorham, Upper Marlboro; Dolores P. Lana, Baltimore, all of Md.

[73] Assignee: The University of Maryland, College Park, Md.

[21] Appl. No.: 61,083

[22] Filed: Jun. 12, 1987

[51] Int. Cl.$^5$ .................... C07K 15/14; C07K 15/28; C12N 15/00; A61K 39/395

[52] U.S. Cl. .................... 530/387; 435/240.27; 435/172.2; 530/395; 530/826; 530/806; 530/809; 424/85.8

[58] Field of Search ............... 530/387; 435/68; 424/89, 85; 935/104

[56] References Cited

U.S. PATENT DOCUMENTS 4,160,024  7/1979  Schat et al. .................... 424/89
4,530,831  7/1985  Lütticken et al. ............... 424/89
4,559,229  12/1985  Page et al. .................... 424/89

FOREIGN PATENT DOCUMENTS 8502545  6/1985  PCT Int'l Appl.

OTHER PUBLICATIONS

Azad et al., In Virology, 149, 190–198, (Mar. 1986).
Kohler et al., Nature, 256, 495–497, (1975).

*Primary Examiner*—Margaret Moskowitz
*Assistant Examiner*—Jeff Kushan
*Attorney, Agent, or Firm*—Oblon, Spivak, McClelland, Maier & Neustadt

[57] ABSTRACT

Monoclonal antibodies effective in preventing infectious bursal disease in chickens, by neutralizing one or more virus strains thereof, have been isolated and obtained from deposited hybridomas. Vaccination of an entire poultry population with a vaccine prepared from these monoclonal antibodies gives a uniform level of protection against all strains of infectious bursal disease tested. The monoclonal antibodies were effective in inducing priming for an active anti-viral response in a heterologous host.

5 Claims, No Drawings

MONOCLONAL ANTIBODY WHICH NEUTRALIZES MULTIPLE STRAINS OF INFECTIOUS BURSAL DISEASE VIRUS

BACKGROUND OF THE INVENTION

1. Field of the Invention

This invention pertains to a method of vaccinating against infectious bursal disease (IBD) in chickens. More specifically, the invention comprises monoclonal antibodies specific to IBD virus (IBDV) which can be effectively employed in a vaccine to prevent the occurrence of this immunosuppressive disease.

2. Background of the Prior Art

Infectious bursal disease (IBD) has been identified as a significant economic drain in the poultry (chiefly, chicken) industry. IBD is caused by virulent field viruses which cause a highly contagious immunosuppressant disease condition, which exacerbates other infections in the chicken population. The disease has the greatest impact on young chickens, and is characterized by lesions in the lymphoidal follicles of the bursa of Fabricius.

As noted, it is particularly young chickens (less than three weeks old) that are most highly susceptible to the virus. These chickens are not yet totally immunologically competent. The conventional forms of treatment to prevent IBD include passive transfer of high levels of maternal antibodies against IBDV from breeder hens to their offspring which may provide temporary protection until the chicks become totally immunologically competent, or through inoculation of the young chicks with a virulent strains of IBDV.

Neither measure is entirely effective, because of the nature of the poultry industry. Specifically, poultry flocks tend to be large aggregations of young broilers obtained from a variety of widely dispersed breeder hen populations. As a result, immunity provided by either of the described methods tends to be both non-uniform, and often inadequate to resist the high challenge doses present in the field from other related strains of the IBDV which may differ from that employed in establishing initial immunity. This lack of uniformity of the level of protection is important because, when the chicks from different breeding groups or single, variable breeder flocks are mixed in a single poultry population, the chicks become susceptible to the effects of IBD at different times, where the level of protection is non-uniform. The result is that not only are some chicks still immune while others are susceptible to field infection, but the immune chicks will not subsequently become vaccinated with the avirulent strains that are normally given at around fourteen days of age. As a result, the chicks which were susceptible at time of vaccination become actively immune, those that were passively immune at the time of vaccination fail to become actively immune and, therefore, predictably, become infected with the field variety of IBDV as soon as maternal antibodies are used up or become critically low.

As is apparent, neither the passive immunization of chicks through the use of maternal antibodies, nor the active immunization achieved by inoculation with avirulent IBDV strains present, is adequate to provide significant protection to all poultry needed to overcome the economic loss represented by IBD.

Accordingly, a need to provide uniform, non-strain specific protection against IBD; specifically, immunity against IBD, without using live virus vaccines which may be adventitious remains a pressing need in the industry.

SUMMARY OF THE INVENTION

Applicants have discovered a novel monoclonal antibody, expressed by a hybridoma prepared through conventional techniques from BALB/c mice injected with various strains of IBDV, which provides high levels of protection against a wide variety of strains of IBD, and is safe for administration to even very young chickens. This neutralizing monoclonal antibody, designated R63, is expressed by the hybridoma cell line deposited at the ATCC under accession no. HB-9490 deposited Aug. 5, 1987. The monoclonal antibody, incorporated in a pharmacologically acceptable carrier, can be used most typically to inoculate one-day-old chicks, and provide uniform, broad strain protection for an entire poultry population against IBD. However, it can also be used on older birds as well. That such a monoclonal antibody (MCA) could exist, having high levels of protection against a variety of strains and that it could be isolated is totally unpredictable from the art, and helps to eliminate some of the noted defects in current methods of dealing with the disease.

The Applicants have also identified a second neutralizing MCA, designated B69, which gives very high levels of protection against a predominant IBDV strain, D78. MCA B69 is expressed by the hybridoma cell line deposited at the ATCC under accession no. HB-9437. A vaccine combining both R63 and B69 gives very high levels of protection against the USDA standard challenge virus and also neutralizes most known and all tested IBDV strains and Serotypes in vitro.

The adminstration of the vaccine of this invention results in a sharp improvement in feed efficiency, and nutritional value of the chickens thus giving a double economic improvement.

As will be recognized by those of skill in the art, having established the neutralizing and binding capacity of the MCAs of this invention it will be apparent that they can be used as the basis for diagnostic assays, and testing for the presence of IBD infection.

The method of isolating the MCAs of this invention is a novel method of identifying potential neutralizing candidates for many diseases and is yet another aspect of this invention.

DETAILED DESCRIPTION OF THE INVENTION

The MCAs of interest herein, R63 and B69, have been demonstrated to give very high levels of protection in field tests against field challenge by IBDV. That such MCAs could be isolated, particularly one such as R63 which confers high levels of in vitro protection against a wide variety of IBDV strains and serotypes, which are known to vary with regard to neutralization sites and characteristics, is entirely unpredictable.

To achieve temporary passive immunization at a uniform, standardized level, and to augment maternally derived levels against IBDV field infection, one-day-old chicks should be vaccinated with a vaccine comprising a pharmacologically acceptable carrier such as phosphate buffered saline, cell culture medium, Mareti's virus vaccine diluent, etc. in which is present an amount of these MCAs effective to provide enhanced protection for a period of time which allows the chicks to become more immunologically competent (about two to three weeks). The necessary levels of protection can be conferred by a single dose of the vaccine administered to day old chicks having a MCA concentration of between 1 microgram and 1 milligram or repeated vaccinations having a smaller effective dose, but carried out over time. If repeated vaccinations are used, the dosage level should range within 10 micrograms to 1 milligram. The concentration level needed to vaccinate older chickens is expected to increase with the weight of the bird.

In a particularly preferred form of the invention, the vaccine incorporates MCAs from both R63 and B69 lines, giving a broader level of neutralization against all strains. As will be appreciated by those of ordinary skill in the art, the actual amount of protection needed, and therefore level of MCA administered through vaccination, will vary from population to population, over time and geographically. Appropriate concentration levels can be determined through routine experimentation, to find appropriate effective levels. Again, what is most important is that the level of protection given be uniform, and sufficient to maintain the birds in an enhanced state of protection until they become more immunologically competent.

Experimental data also suggests that the combined B69 and R63 MCA vaccine also primes the chickens for an active homologous immune response against IBDV. This is achieved by administering between 1 and 1000 micrograms of the vaccine to day-old chickens but not limited to day-old chickens. The MCA vaccine at that dose is not highly immunogenic for young chickens, as little or no detectable immunologic response is observed. However, upon readministration of a similar dose of the vaccine after approximately 6 weeks, a rapid anamnestic type response is made by the chicken against the foreign murine MCAs in the vaccine. Concurrently, a low level active antibody response against IBDV is made by the chicken. The induction of the anti-IBD response in the chicken in the absence of IBD immunization is presumed to be due to the mounting of first an anti-idiotype response to the murine idiotypes of the MCAs by the chicken. This then is followed by an anti-anti idiotype response by the chicken, which is in essence chicken anti-IBDV antibody. Hence, administration of the MCA vaccine can afford a dual measure of protection by passively protecting the chicken and by actively priming the chicken for an immune response to IBDV. That the MCA vaccine could apparently induce priming for an active anti-IBD response in a heterologous host was an unexpected and a unique finding.

By means of illustration only, and without limitation, the method of preparation of the MCAs of the invention claimed herein, and method of identifying suitable MCAs, is set forth hereinbelow. It should be noted that the wide diversity in the amount of protection conferred by any given MCA, and the presence or absence of strain specificity, within the limited hybridoma and MCA population tested and reflected herein (9 different lines) confirms the unexpected nature of the protection conferred by the MCAs claimed herein, R63 and B69.

EXAMPLES

Hybridoma cell lines were prepared according to standard procedure beginning with BALB/c mice, immunized with one virus strain, or a mixture of virus strains (purified). Hybridomas were prepared therefrom and the resulting cell lines were assayed, through an enzyme-linked immunosorbent assay (ELISA) to identify those lines secreting an antibody that binds to at least one strain. The resulting cell lines (9) were cloned again, and injected into pristane primed mice, to produce ascitic fluid with high titer values.

The identified MCA lines, (supernatants containing the selected antibodies) were employed in cross-virus neutralization tests. Only two MCAs, R63 and B69, gave high neutralization values. Accordingly, only these two lines are effective in the preparation of a vaccine giving enhanced, uniform levels of protection against IBD, and are the subject of the claims herein. Additionally, the two MCAs can be combined giving very high protection against IBDV strain D78, and also adequate levels of protection against other strains.

The specific steps taken, persuant to the outline described above, are set forth below.

Propagation of IBDV Strains. All viruses were propagated by inoculating approximately 10,000 tissue culture infective doses ($TCID_{50}$) onto secondary chicken-embryo fibroblast (CEF) monolayers that were prepared from specific-pathogen-free (SPF) embryonating chicken eggs (SPAFAS, Inc., Norwich, Conn.). Virus infected monolayers were frozen and thawed one time after approximately 70% of the monolayer was destroyed. Supernatants were clarified by low speed centrifugation prior to purification on discontinuous sucrose gradients as described (Snyder et al, 1984). Reovirus, strain 1133 (InterVet America, Inc.) which was employed as a control antigen in the ELISA described below was propagated and purified in the same manner.

Production of hybridomas. BALB/c mice were immunized one time (intraperitoneally) 5 to 6 days prior to cell fusions with either the purified D78 virus or with a mixture of purified D78, A/Del, BVM (Serotype I viruses) and OH (Serotype II virus) viruses. Hybridomas were prepared by standard polyethylene glycol-mediated cell fusions that employed immune murine splenocytes and either the X63-Ag.-8.653 or the SP-2/0 murine myeloma cell lines. Nine hybrid cell lines which secreted antibody that bound to at least one IBDV strain in ELISA were cloned three times by limiting dilution. Cloned cell lines were injected into pristane (2,6,10,14-tetramethylpentadecane, Aldrich Chemical Co., Milwaukee, Wis.) primed mice in order to produce high titered ascitic fluid.

ELISA. The ELISA was employed as a screening assay for the isolation of MCAs. In order to equilibrate the screening antigens, titrations were performed on purified virus preparations using 1:200 dilutions of either non-immune chicken sera or monospecific antisera that was prepared in SPF chickens against the D78, A/DEL and BVM IBD strains or against reovirus. This assay method and its rationale have previously been described in detail (Snyder et al, 1985). After equilibration of the purified antigens by using polyclonal chicken antisera, the goat anti-chicken IgG (H+L) conjugate was switched to a goat anti-mouse IgG (H+L) conjugate (Kirkegaard and Perry Laboratories, Gaithersburg, Md.) at a concentration of 1 ug per ml and then the same antigen concentrations were used to screen 1:4 dilutions of the hybridoma supernatants described above. Relative ELISA group titer levels based on a scale of 0 through 9 for supernatants, ascitic fluids and antisera were calculated and reported (Table 1) as described using a regression equation to predict endpoint titers. (Snyder et al, 1985).

Hybridoma supernatants were screened by ELISA beginning around the 17th day post-fusion and cultures of interest were moved into the cloning process. During the course of three fusions nine hybrid cell lines that secreted MCA against IBDV were selected. Two of the fusions used mice primed with D78, while a third fusion utilized mice primed with D78, A/Del, BVM and OH viruses. Relative group ELISA titer levels determined on hybridoma supernatants after the third cloning showed a wide range of reactivity patterns for the MCAs selected (Table 2). Of particular interest was MCA B69 which appeared to be strain specific for D78 and also a group of antibodies which appeared to have nearly exact opposite reactivity patterns e.g., B29 & BK70. MCA R54 appeared to be highly preferential for the A/DEL strain.

Virus neutralization tests with MCAs

Reciprocal-cross micro-VN tests were carried out in secondary CEF cells with 3rd cloning supernatants of the selected MCAs (Table 3) and with ascitic fluids from MCAs B69, BK70 and B29 (Table 4). Results of the VN tests showed that only MCA B69 and R63 neutralized. MCA R63 displayed a high neutralization titer against all IBDV strains tested including the OH serotype II virus and VN titers against all viruses were within 4-fold of each other. Contrariwise, supernatant from MCA B69 displayed high neutralizing activity against only the cloned D78 vaccine strain with nearly a 7-fold difference compared to the next most neutralized strain, which was surprisingly, the OH serotype II virus. A similar neutralization trend was seen with B69 ascitic fluid (Table 4) with nearly a 10-fold difference in neutralization of D78 as compared to other strains.

Since MCAs BK70 and B29 had nearly opposite reactivity patterns in ELISA (Table 2) ascitic fluid containing these MCAs was tested individually and as a pool in VN tests. However, no VN activity was observed with individual or combined pools (Table 4).

Additive virus neutralization tests

Additive VN tests were conducted in order to determine if the combination of MCA B69 and R63 in VN tests would enhance the neutralization observed by the individual MCAs in VN tests against the D78 virus. Results given in Table 5 show that an increase of 4 to 8-fold in VN titer occurs when the B69 and R63 MCAs are used in combination in VN tests.

Agar gel precipition tests

All the MCAs were tested in double immunodiffusion agar gel precipitation tests (AGPT) in order to test their ability to precipitate a commercially available IBD antigen prepared with the 2512 strain of IBD. AGPT analysis showed that only two of the nine MCAs precipitated an antigen in the 2512 bursal antigen preparation and both of those MCAs, R63 and B69, were neutralizing MCAs. The precipitin lines that formed between the R63 and polyclonal control antisera wells fused and created a common precipitin band (as expected with a homogeneous, monomeric antigen). However, no such common precipitin arc formed between the polyclonal antiserum and B69 wells suggests a complexity in the antigen preparation not readily interpretable. The precipitin lines that formed between R63 and B69 wells suggest possible fusion, but the bands formed by the B69 MCA were thickened and would not allow clear definition of a common antigen front.

In vivo experimental protection studies

The ability of the combined R63 and B69 MCAs to protect the cloacal bursa from virulent IBDV challenge was tested experimentally.

Groups of eighteen 1-day old specific-pathogen-free (SPF) white Leghorn chickens that were reared and housed in isolators were inoculated either intraperitoneally (IP) or subcutaneously (SQ) (route not limited to IP or SQ) with 0.2 ml of the combined MCAs, containing a concentration of approximately 20 $\mu$ grams. At day 3 of age, the two inoculated groups and one non-inoculated group were challenged with the USDA standard IBDV challenge (SC-IBD) virus by administering it by bilateral eye drop, two drops of SC-IBD containing $10^{3.8}$ egg infectious doses 50%. Six days later, all three groups of chickens as well as a non-inoculated, non-challenged group were sacrificed and necropsied. Bursa to body weight ratios, body weight and gross bursa size were determined. Both inoculated groups were protected from virulent challenge as demonstrated by gross pathology Table 6.

Experimental induction of an anti-anti idiotypic response

In an experimental trial, six 1-day-old SPF chickens, reared and held in isolation, were passively immunized with the combined R63 and B69 MCAs by intraperitoneal injection of 0.2 ml of this mixture containing approximately 29 $\mu$gm. At 49 days of age, these 6 chicks were bled and then re-innoculated with 0.2 ml of the MCA vaccine. Fourteen days later, both groups were bled, sacrificed and necropsied. The bursa were examined grossly for evidence of accidental IBDV infection. Sera collected were analyzed in ELISA for specific chicken antibodies against IBDV and for antibodies against the combined R63 and B69 MCAs. Results showed that those inoculated chickens responded to the R63 and B69 MCAs after boosting and also concurrently made specific chicken antibody against IBDV (Table 7). This was presumed to be an anti-anti idiotypic response to IBDV as no infection was noted in any of the chickens which were all housed together.

FIELD TESTING

Vaccines prepared from monoclonal antibodies obtained from the procedures described above, now obtainable from hybridoma cell lines ATCC HB-9438 and ATCC HB-9437, were employed in field tests to demonstrate their effectiveness in preventing IBD. Those tests, and the results thereof, are summarized below.

In a field trial, a combination of the two MCAs was used to passively immunize a flock of approximately 7,500 day-old commecial type broiler chickens that were previously determined to have comparatively low levels of maternal antibody against IBDV. By 49-days post-hatch in the field setting, an adjacent house containing a control sister flock experienced typical clinical signs of IBDV field infection, as evidenced by bursal atrophy, whereas the house passively immunized with the combined MCAs showed no such bursal atrophy. The ELISA serology by 35 days post-hatch indicated that both groups were exposed to field IBDV as neither was vaccinated with live or killed IBDV. Hence, the MCA vaccine provided an enhanced level of protection as determined by bursa to body weight ratios. The treated group also finished the study with a significant improvement in feed efficiency, 2.06, as compared to a rating of 1.99 for the controls. This is also confirmed by the nutritional value ratings obtained. The controls had a rating of 16.02. In contrast, the immunized birds had a sharply improved value of 15.70. This difference is an appropriate indication of the value of this invention as confirmed by the fact that the average value, during the testing time period for all flocks of the particular breeder (about 1,000,000 birds) was 15.96, and that for the last 10 growouts of the house where the control birds were grown, had been 0.03 above the average. Thus, the control figure of 16.02 is a reliable figure against which the improvement may be measured.

Obviously, numerous modifications and variations of the present invention are possible in light of the above results. It is therefore to be understood that within the scope of the appended claims, the invention may be practiced otherwise than as specifically described herein.

TABLE 1

Reciprocal-cross ELISAs using chicken antisera prepared against equilibrated IBD virus antigens.

| Antigen[b] | Antisera[a] | | |
|---|---|---|---|
| | D78 | BVM | A/DEL |
| D78 | 5 | 4 | 3 |
| BVM | 4 | 5 | 3 |
| A/DEL | 4 | 4 | 3 |
| 2512 | 4 | 4 | 2 |
| LUK | 3 | 5 | 3 |
| MD | 3 | 4 | 3 |
| OH | 3 | 4 | 2 |
| REO 1133[c] | 0 | 0 | 0 |

[a]ELISA group titers range from 0-9 with each interval equivalent to one two-fold dilution.
[b]ELISA antigens were first equilibrated with a pool of the three antisera.
[c]Reovirus served as a control antigen.

TABLE 2

ELISA reactivity patterns of monoclonal antibodies (MCAs) prepared against strains of IBD virus.

| MCA | VIRUS | | | | | | | |
|---|---|---|---|---|---|---|---|---|
| | D78 | BVM | A/DEL | LUK | 2512 | MD | OH | REO[a] |
| B69 | 9[b] | 0 | 0 | 0 | 0 | 0 | 0 | 0 |
| R63 | 8 | 7 | 7 | 7 | 7 | 7 | 4 | 0 |
| B29 | 9 | 1 | 3 | 3 | 3 | 2 | 1 | 0 |
| BK70 | 2 | 8 | 7 | 7 | 7 | 7 | 4 | 0 |
| 23BK | 2 | 0 | 1 | 0 | 0 | 3 | 0 | 0 |
| B23 | 0 | 2 | 1 | 0 | 0 | 1 | 0 | 0 |
| 8B42 | 0 | 5 | 3 | 0 | 0 | 4 | 1 | 0 |
| 7B26 | 0 | 4 | 1 | 1 | 1 | 1 | 3 | 0 |
| R54 | 0 | 0 | 8 | 0 | 0 | 0 | 2 | 0 |

[a]Reovirus served as the control antigen.
[b]ELISA titers range from 0-9 with each interval being equivalent to one two-fold dilution.

TABLE 3

Reciprocal-cross virus neutralization tests with supernatants of IBD monoclonal antibodies (MCAs).

| MCA | Virus[a] | | | | | | |
|---|---|---|---|---|---|---|---|
| | D78 | LUK | 2512 | BVM | MD | A/DEL | OH |
| B69 | 3,200[b] | 4 | 16 | <4 | <4 | <4 | 32 |
| R63 | 2,048 | 1024 | 512 | 512 | 4196 | 1024 | 1024 |
| B29 | <4 | <4 | <4 | <4 | <4 | <4 | <4 |
| BK70 | <4 | <4 | <4 | <4 | <4 | <4 | <4 |

TABLE 3-continued

Reciprocal-cross virus neutralization tests with supernatants of IBD monoclonal antibodies (MCAs).

| MCA | Virus[a] | | | | | | |
|---|---|---|---|---|---|---|---|
| | D78 | LUK | 2512 | BVM | MD | A/DEL | OH |
| 23BK | <4 | <4 | <4 | <4 | <4 | <4 | <4 |
| B23 | <4 | <4 | <4 | <4 | <4 | <4 | <4 |
| 8B42 | <4 | <4 | <4 | <4 | <4 | <4 | <4 |
| 7B26 | <4 | <4 | <4 | <4 | <4 | <4 | <4 |
| R54 | <4 | <4 | <4 | <4 | <4 | <4 | <4 |

[a]100 TCID of virus was used.
[b]Neutralization titers are the reciprocal of the serum dilution.

TABLE 4

Reciprocal-cross virus neutralization tests with ascitic fluids of IBD monoclonal antibodies (MCAs).

| MCA | D78 | LUK | 2512 | BVM | MD | A/DEL | OH |
|---|---|---|---|---|---|---|---|
| B69 | >2 × 10[6b] | 6400 | 6400 | 100 | 6400 | 400 | 6400 |
| BK70 | <50 | <50 | <50 | <50 | <50 | <50 | <50 |
| B29 | <50 | <50 | <50 | <50 | <50 | <50 | <50 |
| 29 + 70[c] | <50 | <50 | <50 | <50 | <50 | <50 | <50 |

[a]100 TCID of virus was used.
[b]Neutralization titers are the reciprocal of the serum dilution.
[c]Ascitics fluids B29 and BK70 were combined 1:1 and then assayed.

TABLE 5

Additive virus neutralization tests with IBD monoclonal antibodies against the D78 strain of IBD.

| VIRUS[a] | MONOCLONAL ANTIBODY SUPERNATANT | | |
|---|---|---|---|
| | B69 | R63 | B69 + R63[b] |
| D78 | 2,560[c] | 5,120 | 20,480 |

[a]100 TCID of virus was used.
[b]B69 reacted first followed by R63.
[c]Neutralization titers are the reciprocal of the serum dilution.

TABLE 6

Results of in vivo experimental protection studies.

| Treatment | Body wt[1] | Bursa wt[1] | BBWR[1] |
|---|---|---|---|
| NONE | 64 ± 5.2 | .203 ± .04 | .0032 |
| Chall | 61 ± 7.2 | .089 ± .37 | .0015 |
| IP MCAs + Chall | 67 ± 5.9 | .199 ± .04 | .0029 |
| SQ MCAs + Chall | 66 ± 5.7 | .199 ± .06 | .0030 |

[1]N = 18

TABLE 7

Experimental induction of an anti anti-idiotypic response to IBD in chickens by innoculation with the B69 and R63 MCA vaccine.

| Sample[1] | Treatment | Gross Bursa Damage | ELISA Titers[2] | |
|---|---|---|---|---|
| | | | IBDV | MCAs |
| 49 day | None | None | 0 | 0 |
| 49 day | 1 × MCAs | None | 0 | 0 |
| 63 day | None | None | 0 | 0 |
| 63 day | 2 × MCAs | None | 131 | 213 |

[1]6 samples/group
[2]Mean ELISA titer values range from 0-1,900

TABLE 8

Results of field testing using the MCA anti-IBD vaccine

| Age (Days) | Body weight (gm)[1] | | Bursa weight (gm)[1] | | Bursa to Body Weight[1] | | IBD ELISA titer[1,2] | |
|---|---|---|---|---|---|---|---|---|
| | Control | Treated | Control | Treated | Control | Treated | Treated | Control |
| 1 | 38.9 | 38.6 | .047 | .048 | .0012 | .0013 | 3.4 | 3.3 |
| 7 | 119.5 | 122.6 | .28 | .29 | .0028 | .0024 | 1.1 | 0.4 |
| 14 | 281 | 278 | .83 | .87 | .0030 | .0031 | 0 | 0 |

TABLE 8-continued

| | Results of field testing using the MCA anti-IBD vaccine | | | | | | | |
| | Body weight (gm)[1] | | Bursa weight (gm)[1] | | Bursa to Body Weight[1] | | IBD ELISA titer[1,2] | |
| Age (Days) | Control | Treated | Control | Treated | Control | Treated | Treated | Control |
|---|---|---|---|---|---|---|---|---|
| 21 | 511 | 536 | 1.73 | 1.53 | .0034 | .0029 | 0 | 0.3 |
| 28 | 952 | 864 | 1.07 | 2.53 | .0011 | .0029 | 0 | 2.1 |
| 35 | 1365 | 1339 | 1.06 | 2.41 | .0008 | .0018 | 5 | 3.3 |
| 42 | 1836 | 1742 | 1.46 | 1.35 | .0008 | .0008 | 4.2 | 4.8 |
| 49 | 2349 | 2315 | 1.28 | 1.33 | .0005 | .0006 | 4.2 | 5.9 |

[1]Mean of 10 samples
[2]Titer values range from 0 to 9

What is claimed as new and desired to be secured by letters patent of the U.S. is:

1. Hybridomas expressing monoclonal antibodies effective in neutralizing infectious bursal disease virus having the identifying characteristics of the a cell line selected from the group consisting of ATCC HB-9490 and ATCC HB 9437.

2. A monoclonal antibody which binds to and thereby neutralizes at least two strains, or at least one strain and one serotype of infectious bursal disease virus selected form the group consisting of D78, LUK, 2512, BVM, MD, A/DEL and OH serotype II and when said anitbody is admixd with an infectious bursal disease antigen in an agar gel precipitation test, the antibody will precipitate said antigen from an IBDV strain which it neutralizes.

3. The monoclonal antibody of claim 2, wherein said monoclonal antibody has the infectious bursal disease virus neturalizing capability of the monoclonal antibody expressed by hybridoma cell line ATCC HB-9490.

4. The monoclonal antibody claim 3, wherein said monoclonal antibody if the infectious bursal disease virus neturalizing monoclonal antibody expressed by hybridoma cell line ATCC HB-9490.

5. A composition consisting essentially of the antibody of claim 2 or claim 3, together with a pharmaceutically acceptable carrier.

* * * * *